United States Patent
Hwang et al.

(10) Patent No.: US 11,633,342 B2
(45) Date of Patent: Apr. 25, 2023

(54) ADDITIVE COMPOSITION FOR IMPROVING FEEL ON SKIN OF COSMETICS MATERIAL

(71) Applicant: AMOREPACIFIC CORPORATION, Seoul (KR)

(72) Inventors: Yoonkyun Hwang, Yongin-si (KR); Jihye An, Yongin-si (KR); Youngsuk Cho, Yongin-si (KR); Seunghan Park, Yongin-si (KR); Byungfhy Suh, Yongin-si (KR); Byungguen Chae, Yongin-si (KR); Dongwon Choi, Yongin-si (KR); Sanghoon Han, Yongin-si (KR)

(73) Assignee: AMOREPACIFIC CORPORATION, Seoul (KR)

(*) Notice: Subject to any disclaimer, the term of this patent is extended or adjusted under 35 U.S.C. 154(b) by 113 days.

(21) Appl. No.: 16/954,561

(22) PCT Filed: Jan. 9, 2020

(86) PCT No.: PCT/KR2020/000424
§ 371 (c)(1),
(2) Date: Jun. 17, 2020

(87) PCT Pub. No.: WO2020/091584
PCT Pub. Date: May 7, 2020

(65) Prior Publication Data
US 2020/0330355 A1    Oct. 22, 2020

(30) Foreign Application Priority Data
Feb. 14, 2019    (KR) .................. 10-2019-0017334

(51) Int. Cl.
| A61K 8/67 | (2006.01) |
| A61K 8/81 | (2006.01) |
| A61K 8/891 | (2006.01) |
| A61K 8/92 | (2006.01) |
| A61K 8/31 | (2006.01) |
| A61Q 19/00 | (2006.01) |

(52) U.S. Cl.
CPC ............... *A61K 8/676* (2013.01); *A61K 8/31* (2013.01); *A61K 8/671* (2013.01); *A61K 8/678* (2013.01); *A61K 8/8105* (2013.01); *A61K 8/8194* (2013.01); *A61K 8/891* (2013.01); *A61K 8/922* (2013.01); *A61Q 19/00* (2013.01); *A61K 2800/10* (2013.01); *A61K 2800/522* (2013.01); *A61K 2800/59* (2013.01)

(58) Field of Classification Search
None
See application file for complete search history.

(56) References Cited

FOREIGN PATENT DOCUMENTS

| CN | 105120834 A | 12/2015 | |
| CN | 109010120 A | 12/2018 | |
| EP | 3677243 A1 * | 7/2020 | ............ A61Q 19/08 |
| KR | 10-0461458 B1 | 12/2004 | |
| KR | 10-2009-0089372 A | 8/2009 | |
| KR | 10-2010-0121995 A | 11/2010 | |
| KR | 10-2017-0123698 A | 11/2017 | |
| KR | 10-1833040 B1 | 2/2018 | |
| KR | 101833040 B1 * | 2/2018 | ............... A61K 8/03 |
| KR | 10-2018-0116601 A | 10/2018 | |
| WO | WO-0215860 A1 * | 2/2002 | ............ A61K 8/678 |
| WO | 2008/076416 A1 | 6/2008 | |
| WO | 2014/188276 A2 | 11/2014 | |
| WO | 2016/168132 A1 | 10/2016 | |

OTHER PUBLICATIONS

International Search Report of PCT/KR2020/000424 dated Apr. 20, 2020 [PCT/ISA/210].

* cited by examiner

*Primary Examiner* — Dominic Lazaro
(74) *Attorney, Agent, or Firm* — Sughrue Mion, PLLC

(57) ABSTRACT

The present invention relates to an additive composition for cosmetics material containing vitamin-C, the additive composition improving the feel on the skin of vitamin-C which is an anti-oxidant. High vitamin-C content can cause stinging skin irritation or be sticky to the touch, but the additive composition according to the present invention, when used in cosmetics composition with high vitamin-C content, due to the oil, can reduce irritation and stickiness, as well as provide a moisturizing effect.

11 Claims, No Drawings

ADDITIVE COMPOSITION FOR IMPROVING FEEL ON SKIN OF COSMETICS MATERIAL

CROSS REFERENCE TO RELATED APPLICATIONS

This application is a National Stage of International Application No. PCT/KR2020/000424, filed Jan. 9, 2020, claiming priority to Korean Patent Application No. 10-2019-0017334, filed Feb. 14, 2019, the contents of all of which are incorporated herein by reference in their entirety.

TECHNICAL FIELD

The present disclosure relates to an additive composition of a cosmetic composition comprising vitamin C at a high content.

BACKGROUND ART

Vitamin C, a representative antioxidant cosmetic ingredient, has excellent antioxidant effects but is easily denatured by oxygen, heat, pH and the like and causes sticky and irritating feel of use when being used at a high content. Hence, a number of studies has been conducted to overcome this disadvantage.

SUMMARY OF INVENTION

Technical Problem

The technical problem of the present disclosure is to provide an additive composition for a cosmetic composition comprising vitamin C at a high content, which is able to prevent the oxidation of vitamin C and improve the irritating and sticky feel of use when vitamin C is comprised at a high content.

Solution to Problem

The present disclosure provides an additive composition for improving the feel of use of a cosmetic composition comprising vitamin C at 15% by weight or more, which comprises one or more oils selected from the group consisting of dimethicone, methyl trimethicone, hydrogenated C6-14 olefin polymers, diphenylsiloxy phenyl trimethicone, C18-21 alkane, and natural oil.

Advantageous Effects of Invention

The additive composition of the present disclosure is able to improve the tingling and sticky feel of use inherent in vitamin C by being added to a cosmetic composition comprising vitamin C at a high content.

DESCRIPTION OF EMBODIMENTS

As an aspect, the present disclosure may provide an additive composition for improving the feel of use of a cosmetic composition comprising vitamin C at 15% by weight or more. In an embodiment, the additive composition may comprise one or more oils selected from the group consisting of dimethicone, methyl trimethicone, hydrogenated C6-14 olefin polymer, diphenylsiloxy phenyl trimethicone, C18-21 alkane, and natural oil, but the oil is not limited to the oils described above, and oils used in the cosmetic field may be comprised in the additive composition.

An embodiment may provide the use of oil comprising one or more selected from the group consisting of dimethicone, methyl trimethicone, hydrogenated C6-14 olefin polymer, diphenylsiloxy phenyl trimethicone, C18-21 alkane, and natural oil as an active ingredient to be used in the production of an additive for improving the feel of use of a cosmetic composition comprising vitamin C at 15% by weight or more. Another embodiment may provide a method for improving the feel of use of a cosmetic composition comprising vitamin C at 15% by weight or more, which comprises adding oil comprising one or more selected from the group consisting of dimethicone, methyl trimethicone, hydrogenated C6-14 olefin polymer, diphenylsiloxy phenyl trimethicone, C18-21 alkane, and natural oil to a cosmetic composition comprising vitamin C at 15% by weight or more in an effective amount. Another embodiment may provide oil comprising one or more selected from the group consisting of dimethicone, methyl trimethicone, hydrogenated C6-14 olefin polymer, diphenylsiloxy phenyl trimethicone, C18-21 alkane, and natural oil as an active ingredient to be used in an additive for improving the feel of use of a cosmetic composition comprising vitamin C at 15% by weight or more.

In an embodiment, the improvement in the feel of use may comprise one or more of a decrease in stickiness of the cosmetic composition or a decrease in irritating feel of the cosmetic composition.

In an embodiment, the improvement in the feel of use may comprise enhancement of moisturizing feel.

In an embodiment, the natural oil may comprise vegetable oil. In an embodiment, the vegetable oil may comprise one or more selected from the group consisting of meadowfoam seed oil, *Helianthus annuus* (sunflower) seed oil, *Camellia japonica* seed oil, olive oil, grapeseed oil, and *Limnanthes alba* seed oil. In an embodiment, the *Camellia japonica* oil may comprise *Camellia japonica* seed oil. In an embodiment, the *Camellia japonica* oil may comprise fermented *Camellia japonica* oil. In an embodiment, the oil may comprise one or more of dimethicone or methyl trimethicone; and natural oil.

In an embodiment, the additive composition may further comprise squalane and a fat-soluble antioxidant substance.

In an embodiment, the fat-soluble antioxidant substance may be a fat-soluble antioxidant substance to be used in a cosmetic composition and may comprise, for example, one or more selected from the group consisting of tocopherol, lycopene, and retinol.

In an embodiment, the oil may be comprised as a double layer formed of a first oil layer and a second oil layer. In an embodiment, the first oil layer may be an oil to be used in cosmetics but may comprise, for example, one or more oils selected from the group consisting of dimethicone, methyl trimethicone, hydrogenated C6-14 olefin polymer, diphenylsiloxy phenyl trimethicone, C18-21 alkane, and natural oil. In an embodiment, the second oil layer may be an oil layer covering the surface of the first oil layer and may comprise vegetable oil.

In an embodiment, the vegetable oil in the second oil layer may be vegetable oil to be used in cosmetics but may comprise, for example, one or more selected from the group consisting of meadowfoam seed oil, *Helianthus annuus* (sunflower) seed oil), *Camellia japonica* seed oil, olive oil, grapeseed oil, and *Limnanthes alba* seed oil.

In an embodiment, the additive composition may not comprise a surfactant.

In an embodiment, the content of vitamin C in the cosmetic composition may be 15% to 35% by weight with respect to the total weight of the cosmetic composition. Specifically, the content of vitamin C may be 15% by weight or more, 18% by weight or more, 20% by weight or more, 21% by weight or more, 22% by weight or more, 23% by weight or more, 24% by weight or more or 25% by weight or more and 35% by weight or less, 32% by weight or less, 30% by weight or less, 29% by weight or less, 28% by weight or less, 27% by weight or less or 26% by weight or less with respect to the total weight of the cosmetic composition.

In an embodiment, the content of the additive composition may be 3% to 50% by weight based on the total weight of the cosmetic composition. Specifically, the content of the additive composition may be 3% by weight or more, 8% by weight or more, 13% by weight or more, 18% by weight or more, 19% by weight or more, 20% by weight or more, 21% by weight or more, 22% by weight or more, 23% by weight or more, 24% by weight or more or 25% by weight or more and 50% by weight or less, 45% by weight or less, 40% by weight or less, 35% by weight or less, 30% by weight or less, 29% by weight or less, 28% by weight or less, or 27% by weight or less or 26% by weight or less based on the total weight of the cosmetic composition. More specifically, the content of the additive composition may be 3% by weight or more, 4% by weight or more, 5% by weight or more, 6% by weight or more or 7% by weight or more and 12% by weight or less, 11% by weight or less, 10% by weight or less, 9% by weight or less or 8% by weight or less based on the total weight of the cosmetic composition.

In an embodiment, the weight ratio of the first oil layer:the second oil layer may be 30:1 to 1:30. Specifically, the weight ratio may be 27:1 or more, 24:1 or more, 21:1 or more, 18:1 or more, 15:1 or more, 12:1 or more, 9:1 or more, 8:1 or more, 7:1 or more, 6:1 or more, 5:1 or more, 4.5:1 or more, 4:1 or more, 3.5:1 or more, 3:1 or more, 2.5:1 or more, 2:1 or more or 1.5:1 or more and 1:30 or less, 1:27 or less, 1:24 or less, 1:21 or less, 1:18 or less, 1:15 or less, 1:12 or less, 1:9 or less, 1:8 or less, 1:7 or less, 1:6 or less, 1:5 or less, 1:4.5 or less, 1:4 or less, 1:3.5 or less, 1:3 or less, 1:2.5 or less or 1:2 or less. More specifically, the weight ratio of the first oil layer:the second oil layer may be 2:1 or more, 1.9:1 or more, 1.8:1 or more, 1.5:1 or more, 1.4:1 or more, 1.3:1 or more, 1.2:1 or more or 1.1:1 or more and 1:1.9 or less, 1:1.8 or less, 1:1.7 or less, 1:1.6 or less, 1:1.5 or less, 1:1.4 or less, 1:1.3 or less or 1:1.2 or less.

EMBODIMENTS

Hereinafter, the present invention will be described in more detail with reference to Examples. These Examples are only for illustrating the present invention, and it will be apparent to those skilled in the art that the scope of the present invention is not to be construed as limited by these Examples.

Evaluation of Skin Irritation and Feel of Use Depending on Presence or Absence of Oil The evaluation test on the skin irritation and feel of use was performed in Comparative Examples 1 to 3 and Examples 1 to 7 of Table 1 below.

TABLE 1

| INCI | Comparative Example 1 | Comparative Example 2 | Comparative Example 3 | Example 1 | Example 2 |
|---|---|---|---|---|---|
| Water | To 100 | To 100 | To 100 | To 100 | To 100 |
| Disodium EDTA | 0.05 | 0.05 | 0.05 | 0.05 | 0.05 |
| Propanediol | 10 | 10 | 10 | 10 | 10 |
| Ascorbic acid (vitamin c) | 25 | 25 | 25 | 25 | 25 |
| Acid yellow 23 | 0.0007 | 0.0007 | 0.0007 | 0.0007 | 0.0007 |
| Glutathione | 0.1 | 0.1 | 0.1 | 0.1 | 0.1 |
| Sodium hyaluronate | 0.4 | 0.4 | 0.4 | 0.4 | 0.4 |
| Cetyl 2-ethyl hexanoate | — | 5 | — | — | — |
| Dimethicone | — | — | — | 5 | 2.5 |
| Methyl trimethicone | — | — | — | — | — |
| Helianthus Annuus (sunflower) seed oil | — | — | — | — | 1.85 |
| Meadowfoam seed oil | — | — | — | — | — |
| Camellia japonica seed oil | — | — | — | — | — |
| Squalane | — | — | 5 | — | — |
| Tocopherol | — | — | — | 0.5 | 0.5 |
| Solanum lycopersicum (tomato) fruit lipids | — | — | — | 0.00.5 | 0.00.5 |
| Fragrance | — | 0.15 | 0.15 | 0.15 | 0.15 |

TABLE 1-continued

| INCI | Example 3 | Example 4 | Example 5 | Example 6 | Example 7 |
|---|---|---|---|---|---|
| Water | To 100 | To 100 | To 100 | To 100 | To 100 |
| Disodium EDTA | 0.05 | 0.05 | 0.05 | 0.05 | 0.05 |
| Propanediol | 20 | 10 | 10 | 10 | 10 |
| Ascorbic acid (vitamin c) | 25 | 25 | 25 | 25 | 25 |
| Acid yellow 23 | 0.0007 | 0.0007 | 0.0007 | 0.0007 | 0.0007 |
| Glutathione | 0.1 | 0.1 | 0.1 | 0.1 | 0.1 |
| Sodium hyaluronate | 0.4 | 0.4 | 0.4 | 0.4 | 0.4 |
| Cetyl 2-ethyl hexanoate | — | — | — | — | — |
| Dimethicone | 2.5 | — | 2.5 | 2.5 | — |
| Methyl trimethicone | — | 5 | — | — | 2.5 |
| Helianthus Annuus (sunflower) seed oil | — | — | — | — | 1.85 |
| Meadowfoam seed oil | — | — | 1.85 | — | — |
| Camellia japonica seed oil | — | — | — | 1.85 | — |
| Squalane | 1.85 | — | — | — | — |
| Tocopherol | 0.5 | 0.5 | — | — | — |
| Solanum lycopersicum (tomato) fruit lipids | 0.00.5 | 0.00.5 | 0.00.5 | 0.00.5 | 0.00.5 |
| Fragrance | 0.15 | 0.15 | 0.15 | 0.15 | 0.15 |

(1) Evaluation on Skin Irritation

In order to evaluate skin irritation degree of the cosmetic composition, a skin patch test was performed with 20 healthy men and women in their twenties to forties. The composition in Table 1 was shaken, mixed, and then patched on the back to perform a skin patch test at 20 μl/chamber for 48 hours. The patch was attached for 1 hour and removed, then the skin irritation degree was evaluated at the 24th hour and 48th hour, and the results are presented in Table 3 below. Table 2 is a score table of skin irritation scale.

TABLE 2

| Division | Skin irritation |
|---|---|
| 0 | Non-irritating |
| 1 | Very slightly irritating |
| 2 | Slightly irritating |
| 3 | Moderately irritating |
| 4 | Strongly irritating |

TABLE 3

| Skin irritation index | 24 h | | | | | 48 h | | | | |
|---|---|---|---|---|---|---|---|---|---|---|
| | 0 | 1 | 2 | 3 | 4 | 0 | 1 | 2 | 3 | 4 |
| Comparative Example 1 | 13 | 5 | 2 | 0 | 0 | 12 | 7 | 1 | 0 | 0 |
| Comparative Example 2 | 13 | 6 | 1 | 0 | 0 | 16 | 3 | 1 | 0 | 0 |
| Comparative Example 3 | 18 | 2 | 0 | 0 | 0 | 20 | 0 | 0 | 0 | 0 |
| Example 1 | 18 | 2 | 0 | 0 | 0 | 20 | 0 | 0 | 0 | 0 |
| Example 2 | 17 | 2 | 1 | 0 | 0 | 20 | 0 | 0 | 0 | 0 |
| Example 3 | 18 | 2 | 0 | 0 | 0 | 20 | 0 | 0 | 0 | 0 |
| Example 4 | 18 | 2 | 0 | 0 | 0 | 20 | 0 | 0 | 0 | 0 |
| Example 5 | 17 | 2 | 1 | 0 | 0 | 20 | 0 | 0 | 0 | 0 |
| Example 6 | 18 | 2 | 0 | 0 | 0 | 20 | 0 | 0 | 0 | 0 |
| Example 7 | 18 | 2 | 0 | 0 | 0 | 20 | 0 | 0 | 0 | 0 |

Comparative Example 1 is an example in which oil is not used, and a large number of people felt skin irritation. Comparative Example 2 is an example in which cetyl 2-ethylhexanoate was used, and even though oil was comprised, the number of people who felt skin irritation was similar to that in Comparative Example 1 in which an oil layer was not comprised. However, the number of people who felt skin irritation in Examples 1 to 7 was remarkably smaller than that in Comparative Examples 1 and 2. This indicates that the degree of skin irritation varies depending on the kind of oil as well as the presence or absence of oil.

(2) Sensory Evaluation

The evaluation on the moisturizing feel and stickiness was performed with 20 women in their twenties to thirties. A composition comprising vitamin C and an oil layer was shaken, mixed, and then applied to the skin to perform the evaluation. The sensory evaluation was performed by a five-point scale method, and the results are presented in Table 4 below.

TABLE 4

| | Comparative Example 1 | Comparative Example 2 | Comparative Example 3 | Example 1 | Example 2 | Example 3 | Example 4 | Example 5 | Example 6 | Example 7 |
|---|---|---|---|---|---|---|---|---|---|---|
| Moisturizing feel | 1.85 | 2.75 | 4.6 | 4.6 | 4.5 | 4.6 | 3 | 4.25 | 4.15 | 4.2 |
| Stickiness | 2.05 | 4.2 | 4.6 | 4.65 | 4.55 | 4.65 | 4.25 | 4.55 | 4.1 | 4.15 |
| Freshness | 1.9 | 4.3 | 3.35 | 3.9 | 3.65 | 3.6 | 4.7 | 3.7 | 3.4 | 3.85 |

The evaluation criteria were as follows: 5 points for significantly excellent, 4 points for excellent, 3 points for normal, 2 points for poor, and 1 point for significantly poor. In the case of stickiness evaluation, it was evaluated as 5 points when the composition feels less sticky and as 1 point the composition feels stickier. The freshness was evaluated as 5 points when the composition feels fresher and as 1 point when the composition feels less fresh.

In the case of vitamin C, the composition feels stickier as the content thereof in the composition is higher. Hence, in the case of Comparative Example 1 in which an oil layer was not comprised, the freshness was significantly low and stickiness was high. In the case of Comparative Example 2, the moisturizing feel was insufficient. In the case of Comparative Example 3, moisturizing feel and stickiness similar to those in Examples 1 to 4 were exhibited but the freshness was evaluated to be low. However, from Table 4 above, it can be seen that, in Examples 1 to 7, not only moisturizing feel is excellent but also the sticky feel of use is remarkably decreased and still fresher feel of use than in Comparative Examples is exerted. Particularly, in the case of Example 4, the composition was evaluated to provide significantly high freshness and it has been found that the composition has an excellent effect of improving the unpleasant feel of use of vitamin C that feels heavy and thick.

Consequently, from the comprehensive results of the skin irritation test and sensory test, it has been found that an oil layer should be comprised and the kind of oil should be also selected and used as in the present disclosure in order to decrease the irritation degree of vitamin C and improve the sticky feel of use, which are the purpose of the present invention.

In addition, in a case in which the contents of additives for improving the feel of use of cosmetic compositions comprising antioxidant substances in the same amount increase, the contents of ingredients to be comprised to prevent the precipitation of antioxidant substances such as vitamin C inevitably decrease. When dimethicone or methyl trimethicone and natural oil are used in mixture, the skin irritation is low, favorable feel of use is provided, the amounts of additives are decreased, and it is thus possible to provide a product comprising an antioxidant substance at a high content.

The present invention can provide the following embodiments as an aspect.

The first embodiment may provide an additive composition for improving feel of use of a cosmetic composition comprising vitamin C at 15% by weight or more, which comprises one or more selected from the group consisting of dimethicone, methyl trimethicone, hydrogenated C6-14 olefin polymer, diphenylsiloxy phenyl trimethicone, C18-21 alkane, and natural oil.

The second embodiment may provide the additive composition according to the first embodiment, in which the improvement in feel of use comprises one or more of a decrease in stickiness of the cosmetic composition or a decrease in irritating feel of the cosmetic composition.

The third embodiment may provide the additive composition according to one or more of the first embodiment or second embodiment, in which the improvement in feel of use comprises enhancement of moisturizing feel.

The fourth embodiment may provide the additive composition according to one or more of the first embodiment to the third embodiment, in which the natural oil comprises one or more selected from the group consisting of meadowfoam seed oil, *Helianthus annuus* (sunflower) seed oil, *Camellia japonica* seed oil, olive oil, grapeseed oil, and *Limnanthes alba* seed oil.

The fifth embodiment may provide the additive composition according to one or more of the first embodiment to the fourth embodiment, in which the additive further comprises squalane and a fat-soluble antioxidant substance.

The sixth embodiment may provide the additive composition according to one or more of the first embodiment to the fifth embodiment, in which the fat-soluble antioxidant substance comprises one or more selected from the group consisting of tocopherol, lycopene, and retinol.

The seventh embodiment may provide the additive composition according to one or more of the first embodiment to the sixth embodiment, in which the oil is comprised as a double layer formed of a first oil layer and a second oil layer, in which the first oil layer comprises one or more oils selected from the group consisting of dimethicone, methyl trimethicone, hydrogenated C6-14 olefin polymer, diphenylsiloxy phenyl trimethicone, C18-21 alkane, and natural oil, and the second oil layer is an oil layer covering a surface of the first oil layer and comprises vegetable oil.

The eighth embodiment may provide the additive composition according to one or more of the first embodiment to the seventh embodiment, in which the vegetable oil in the second oil layer comprises one or more selected from the group consisting of meadowfoam seed oil, *Helianthus annuus* (sunflower) seed oil), *Camellia japonica* seed oil, olive oil, grapeseed oil, and *Limnanthes alba* seed oil.

The ninth embodiment may provide the additive composition according to one or more of the first embodiment to the eighth embodiment, in which a content of vitamin C in the cosmetic composition is 15% to 35% by weight with respect to a total weight of the cosmetic composition.

The tenth embodiment may provide the additive composition according to one or more of the first embodiment to the ninth embodiment, in which the additive composition is comprised at 3% to 12% by weight based on a total weight of the cosmetic composition.

The eleventh embodiment may provide the additive composition according to one or more of the first embodiment to the tenth embodiment, in which a weight ratio of the first oil layer:the second oil layer is 30:1 to 1:30.

The twelfth embodiment may provide the additive composition according to one or more of the first embodiment to the eleventh embodiment, in which the oil comprises one or more of dimethicone or methyl trimethicone; and natural oil.

The invention claimed is:

1. A method for improving feel of use of a cosmetic composition, which comprises adding an additive composition comprising methyl trimethicone or a combination of dimethicone and methyl trimethicone, to the cosmetic composition in an effective amount,
    wherein the cosmetic composition comprises vitamin C in an amount of 15% by weight or more based on total weight of the cosmetic composition,
    wherein the improvement in feel of use comprises one or more of a decrease in stickiness of the cosmetic composition or a decrease in irritating feel of the cosmetic composition, and
    wherein the stickiness and irritating feel of the cosmetic composition are caused by vitamin C of an amount of 15% by weight or more based on total weight of the cosmetic composition.

2. The method according to claim 1, wherein the improvement in feel of use further comprises enhancement of moisturizing feel.

3. The method according to claim 1, wherein the additive composition further comprises squalane and a fat-soluble antioxidant substance.

4. The method according to claim 3, wherein the fat-soluble antioxidant substance comprises one or more selected from the group consisting of tocopherol, lycopene, and retinol.

5. The method according to claim 1, wherein the oil is comprised as a double layer formed of a first oil layer and a second oil layer, wherein
    the first oil layer comprises methyl trimethicone or the combination of dimethicone and methyl trimethicone, and
    the second oil layer comprises a second oil and covers a surface of the first oil layer, wherein the second oil comprises a vegetable oil.

6. The method according to claim 5, wherein the vegetable oil in the second oil layer comprises one or more selected from the group consisting of meadowfoam seed oil, *Helianthus annuus* (sunflower) seed oil, *Camellia japonica* seed oil, olive oil, grapeseed oil, and *Limnanthes alba* seed oil.

7. The method according to claim 5, wherein a weight ratio of the first oil layer:the second oil layer is 30:1 to 1:30.

8. The method according to claim 1, wherein a content of vitamin C in the cosmetic composition is 15% to 35% by weight based on the total weight of the cosmetic composition.

9. The method according to claim 1, wherein the additive composition is added at 3% to 12% by weight based on the total weight of the cosmetic composition.

10. A method for improving feel of use of a cosmetic composition, said method comprising adding an effective amount of an additive composition to the cosmetic composition,
    wherein the cosmetic composition comprises vitamin C at 15% by weight or more based on total weight of the cosmetic composition, and
    wherein the additive composition comprises methyl trimethicone or a combination of dimethicone and methyl trimethicone, and additionally one or more selected from the group consisting of hydrogenated $C_{6-14}$ olefin polymer, diphenylsiloxy phenyl trimethicone, $C_{18-21}$ alkane, and a natural oil,
    wherein the improvement in feel of use comprises one or more of a decrease in stickiness of the cosmetic composition or a decrease in irritating feel of the cosmetic composition, and
    wherein the stickiness and irritating feel of the cosmetic composition are caused by vitamin C of an amount of 15% by weight or more based on total weight of the cosmetic composition.

11. The method according to claim 10, wherein the natural oil comprises one or more selected from the group consisting of meadowfoam seed oil, *Helianthus annuus* (sunflower) seed oil, *Camellia japonica* seed oil, olive oil, grapeseed oil, and *Limnanthes alba* seed oil.

* * * * *